US007683177B2

(12) United States Patent
Braude et al.

(10) Patent No.: US 7,683,177 B2
(45) Date of Patent: Mar. 23, 2010

(54) PROCESS FOR PREPARING 2-[(PYRIDINYL)METHYL]SULFINYL-SUBSTITUTED BENZIMIDAZOLES AND NOVEL CHLORINATED DERIVATIVES OF PANTOPRAZOLE

(75) Inventors: Viviana Braude, Kadima (IL); Nina Finkelstein, Herzliya (IL); Kobi Chen, Ramat HaSharon (IL); Gideon Pilarsky, Holon (IL); Anita Liberman, Tel-Aviv (IL); Claude Singer, Kfar Saba (IL); Yuriy Raizi, Natanya (IL)

(73) Assignee: Teva Pharmaceutical Industries Ltd, Petah Tiqva (IL)

( * ) Notice: Subject to any disclaimer, the term of this patent is extended or adjusted under 35 U.S.C. 154(b) by 0 days.

(21) Appl. No.: 10/866,261

(22) Filed: Jun. 10, 2004

(65) Prior Publication Data

US 2005/0075370 A1 Apr. 7, 2005

Related U.S. Application Data

(60) Provisional application No. 60/477,045, filed on Jun. 10, 2003, provisional application No. 60/525,851, filed on Dec. 1, 2003.

(51) Int. Cl.
*C07D 401/12* (2006.01)
(52) U.S. Cl. .................................. 546/273.7
(58) Field of Classification Search ............... 546/273.7
See application file for complete search history.

(56) References Cited

U.S. PATENT DOCUMENTS

| 4,508,905 | A |   | 4/1985  | Schwartz et al. |
| 4,555,518 | A |   | 11/1985 | Rainer et al. |
| 4,628,098 | A |   | 12/1986 | Nohara et al. |
| 4,758,579 | A | * | 7/1988  | Kohl et al. ................. 514/338 |
| 5,045,552 | A |   | 9/1991  | Souda et al. |
| 5,391,752 | A |   | 2/1995  | Hoerrner et al. |
| 5,708,013 | A |   | 1/1998  | Shimomura et al. |
| 6,017,560 | A |   | 1/2000  | Hirai et al. |
| 6,313,303 | B1 |  | 11/2001 | Tagami et al. |
| 6,410,569 | B1 |  | 6/2002  | Kohl |
| 6,423,846 | B1 |  | 7/2002  | Moon et al. |
| 6,545,024 | B1 |  | 4/2003  | Tsujii et al. |
| 6,686,379 | B2 |  | 2/2004  | Kohl |
| 6,723,852 | B2 | * | 4/2004 | Berenguer Maimo .... 546/273.4 |
| 6,919,459 | B2 |  | 7/2005  | Broeckx et al. |
| 6,933,389 | B2 |  | 8/2005  | Reddy et al. |
| 6,998,490 | B2 |  | 2/2006  | Allegrini et al. |
| 7,060,839 | B2 |  | 6/2006  | Palomo |
| 7,064,213 | B1 |  | 6/2006  | Chen |
| 7,064,214 | B2 |  | 6/2006  | Senanayake et al. |
| 7,081,534 | B2 |  | 7/2006  | Napoletano et al. |
| 7,105,681 | B2 |  | 9/2006  | Turchetta et al. |
| 7,129,358 | B2 |  | 10/2006 | Avrutov et al. |
| 7,176,319 | B2 |  | 2/2007  | Reddy et al. |
| 7,294,716 | B2 |  | 11/2007 | Garst et al. |
| 2003/0036554 | A1 |   | 2/2003 | Avrutov et al. |
| 2003/0036656 | A1 | * | 2/2003 | Maimo ..................... 546/273.7 |
| 2004/0138466 | A1 | * | 7/2004 | Avrutov et al. ........... 546/273.7 |
| 2004/0158072 | A1 |   | 8/2004 | Loebermann et al. |
| 2004/0177804 | A1 | * | 9/2004 | Finkelstein et al. ........... 117/94 |
| 2004/0186139 | A1 |   | 9/2004 | Reddy et al. |
| 2004/0235904 | A1 | * | 11/2004 | Finkelstein et al. ......... 514/338 |
| 2005/0075370 | A1 |   | 4/2005 | Braude et al. |
| 2005/0288334 | A1 |   | 12/2005 | Kohl et al. |
| 2006/0089386 | A1 |   | 4/2006 | Reddy et al. |
| 2006/0128767 | A1 |   | 6/2006 | Senanayake et al. |
| 2006/0167262 | A1 |   | 7/2006 | Kohl et al. |
| 2007/0082929 | A1 |   | 4/2007 | Rogers et al. |
| 2007/0185093 | A1 |   | 8/2007 | Buck et al. |
| 2007/0225500 | A1 |   | 9/2007 | Kohl et al. |
| 2008/0076929 | A1 |   | 3/2008 | Reddy et al. |
| 2009/0005570 | A1 |   | 1/2009 | Fan |

FOREIGN PATENT DOCUMENTS

CA          1254215          5/1989

(Continued)

OTHER PUBLICATIONS

Moustafa, "Spectrophotometric methods for the, etc.," Journal of Pharmaceutical and Biomedical Analysis, 22 (2000) 45-58.*
A. Badwan et al. "Pantoprazole Sodium" in Analytical Profiles of Drugs Substances and Excipients (Brittain H G, Editor, Academic Press, Amsterdam), Paragraph '03.4, Table I; vol. 29, 2002, p. 213-259.
Brittain et al., "Polymorphism in Pharmaceutical Solids" NY: Marcel Dekker (1999). pp. 1-2 and 185.
Concise Encyclopedia Chemistry, pp. 872-873 (1993).
Drabowicz et al., Synthesis of Sulphoxides; Rappoport et al. The Synthesis of Sulphones and Sulphoxides. p. 249 (J. Wiley & Sons: New York 1988).

(Continued)

*Primary Examiner*—Patricia L Morris
(74) *Attorney, Agent, or Firm*—Kenyon & Kenyon LLP (57) ABSTRACT

The present invention provides a process comprising admixing a thioether with about 1.05 to about 1.6 molar equivalents of an active chlorine-containing oxidant, preferably sodium hypochlorite, and about 2.5 to about 5.0 molar equivalents of an alkali metal base; and recovering a sulfoxide that is preferably pantoprazole, lansoprazole, omeprazole, or rabeprazole. The process may further comprise contacting the sulfoxide with a source of sodium ions, preferably sodium hydroxide, to produce the sodium salt of the sulfoxide. The invention also relates to novel chlorinated derivatives of pantoprazole including 5-(difluoromethoxy)-2-[[(3,4-dimethoxy-2-pyridinyl)-chloromethyl]sulfinyl]-1H-benzimidazole and 5-(difluoromethoxy)-2-[[(3,4-dimethoxy-2-pyridinyl)-chlorohydroxymethyl]sulfinyl]-1H-benzimidazole and processes for making them. The invention also relates to processes of quantifying and identifying a compound other than pantoprazole in a mixture of pantoprazole and at least one other compound.

8 Claims, 7 Drawing Sheets

FOREIGN PATENT DOCUMENTS

| | | |
|---|---|---|
| DE | 40 35 455 | 5/1992 |
| EP | 0 134 400 | 3/1985 |
| EP | 302720 | 2/1989 |
| EP | 484265 A | 5/1992 |
| EP | 0 533 264 | 3/1993 |
| EP | 0533790 | 3/1993 |
| EP | 0997461 | 5/2000 |
| EP | 1 270 555 | 1/2003 |
| EP | 1 306 375 | 5/2003 |
| EP | 1575941 | 3/2005 |
| ES | 860 2765 | 3/1986 |
| ES | 860 4929 | 8/1986 |
| ES | 870 3868 | 5/1987 |
| ES | 2246151 | 2/2006 |
| GB | 2 134 523 | 8/1984 |
| WO | WO 91/19710 | 12/1991 |
| WO | WO 96/02535 | 2/1996 |
| WO | WO 96/17607 | 6/1996 |
| WO | WO 97/29103 | 8/1997 |
| WO | WO 98/40377 | 9/1998 |
| WO | WO 98/40378 | 9/1998 |
| WO | WO 99/47514 | 9/1999 |
| WO | WO 00/10995 | 3/2000 |
| WO | WO 01/004109 | 1/2001 |
| WO | WO 01/021617 | 3/2001 |
| WO | WO 2001/083473 | 11/2001 |
| WO | WO 02/28852 | 4/2002 |
| WO | WO 02/062786 | 8/2002 |
| WO | WO 03/008406 | 1/2003 |
| WO | 03/062223 * | 7/2003 |
| WO | WO 2003/062223 | 7/2003 |
| WO | WO 2003/097606 | 11/2003 |
| WO | WO 2004/013126 | 2/2004 |
| WO | WO 04/063188 | 7/2004 |
| WO | WO 2004/085424 | 10/2004 |
| WO | WO 2004/099183 | 11/2004 |
| WO | WO 05/077936 | 8/2005 |
| WO | WO 2006/019151 | 2/2006 |
| WO | WO 2006/040635 | 4/2006 |
| WO | WO 2006/040778 | 4/2006 |
| WO | WO 2006/064249 | 6/2006 |
| WO | WO 2006/100243 | 9/2006 |
| WO | WO 07/026188 | 3/2007 |
| WO | WO 07/036771 | 4/2007 |
| WO | WO 07/041790 | 4/2007 |
| WO | WO 2007/066202 | 6/2007 |
| WO | WO 2007/068925 | 6/2007 |
| WO | WO 07/086077 | 8/2007 |
| WO | WO 2007/091276 | 8/2007 |
| WO | WO 2008/001392 | 1/2008 |
| WO | WO 2008/017020 | 2/2008 |

OTHER PUBLICATIONS

Gamer A et al: "Pantoplazole: A New and More Specific Proton Pump Inhibitor", Expert Opinion on investigational Drugs, Ashley Publications Ltd., London, GB, vol. 6, No. 7, 1997, pp. 885-893.

Graul A et al: "Esomeprazone Magnesium(–)-Omeprazole Magnesium Perprazole (formerly) (S)-Omeprazole Magnesium H-199/18 Nexium", Drugs of the Future, Barcelona, ES, vol. 24, No. 11, 1999, pp. 1178-1183.

Halebian et al., "Pharmaceutical Applications of Polymorphisim" J of Pharm. Sci, 58 (8) 1969 pp. 911-929.

Jain et al., "Polymorphism in Pharmacy" Indian Drugs, 1986, 23 (6) pp. 315-329.

Kohl B. et al.: "(H+, K+)-ATPase inhibiting 2-[(2-pyridylemthyl)Sulfinyl] Benzimidazoles. 4. A novel Series of Dimethoxypyridyl-substituted inhibitors with enhanced selectivity. The selection of Pantoprazole as a clinical candidate" Journal of Medicinal Chemistry, American Chemical Society, vol. 35, No. 6, 1992, pp. 1049-1057.

Kotar-Jordan, B. "Solid State Characterization of New Pantoprazole Sodium Hydrate Forms" Farm. Vestn., pp. 411-412, vol. 54, No. 2, 2003.

Muzaffar et al., "Polymorphism and drug availability," J of Pharmacy (Lahore), 1979, 1(1), pp. 59-66.

Otsuka et al., "Effect of Polymorphic Forms of Bulk Powders on Pharmaceutical Properties of Carbamazepine Granules," Chem. Pharm. Bull. 47(6) 852-856 (1999).

Rouhi et al, "The Right Stuff," Chemical & Engineering News. Feb 2003, pp. 32-35.

Taday et al., "Using Terahertz Pulse Spectroscopy to Study the Crystalline Structure of Drug: A Case Study of the Polymorphs of Ranitidine Hydrochloride," J of Pharmaceutical Sciences, 92 (4), Apr. 2003, pp. 831-838.

Ulicky et al., "Comprehensive Dictionary of Physical Chemistry" NY: PTR Prentice Hall (1992) p. 21.

U.S. Pharmacopia #23, 1995, pp. 1843-1844.

Vyas K et al. "Lansoprazole, An Antiulcerative Drug", Acta Crystalographica Section C. Crystal Structure Communications, Munksgaard, Copenhagen, DK, vol. C56, No. 12, 2000, pp. E572-E573.

Williams M P et al: "Review Article: The Pharmacology of Rabeprazole" Alimentary Pharmacology & Therapeutics, Blackwell Scientific Publications LTD., Cambridge, GB, vol. 13, No, 1999, pp. 3-10.

Third Party Observation, dated Jun. 17, 2009, from corresponding European Patent Application No. 0700422.5 filed Mar. 1, 2007.

Third Party Observation, dated Jan. 30, 2008, from corresponding European Patent Application No. 04755278.1 filed Jun. 10, 2004.

Third Party Observation, dated Jun. 3, 2008, from corresponding European Patent Application No. 04755278.1 filed Jun. 10, 2004.

Badwan, A. et al. "Pantoprazole Sodium" *Analytical Profiles of Drugs Substances and Excipients*, vol. 29, No. 1, pp. 213-259 (2002).

Doelker, English translation of S.T.P. Pratiques (1999), 9(5), 399-409, pp. 1-33.

Doelker et al., CA 132 :325872, 2000.

Drabowicz et al., Organic Preparations and Procedures Int. 14(1-2), 45-89 (1982).

Merck Index, 13th ed., p. 1256, compound 7084 (2001).

Reddy et al., "Preparation of Amorphous Form of Anti Ulcer Drugs," *Rasayan Journal of Chemistry*, 1(1): 166-170 (2008).

Toribio et al., " Semipreparative chiral supercritical fluid chromatography in the fractionation of lansoprazole and two related antiulcer drugs enantiorrers," *Journal of Separation Science*, 31: 1307-1313 (2008).

* cited by examiner

PROCESS FOR PREPARING 2-[(PYRIDINYL)METHYL]SULFINYL-SUBSTITUTED BENZIMIDAZOLES AND NOVEL CHLORINATED DERIVATIVES OF PANTOPRAZOLE

PRIORITY

This application claims the benefit of U.S. Provisional Application Ser. No. 60/477,045 filed Jun. 10, 2003 and U.S. Provisional Application Ser. No. 60/525,851 filed Dec. 1, 2003, both of which are incorporated herein by reference.

FIELD OF THE INVENTION

The present invention relates to a process for preparing 2-[(pyridinyl)methyl]sulfinyl-substituted benzimidazoles by oxidation of a 2-[(pyridinyl)methyl]thio-substituted benzimidazole and to certain chlorinated derivatives of pantoprazole.

BACKGROUND OF THE INVENTION

Certain 2-[(pyridinyl)methyl]sulfinyl-substituted benzimidazoles whose molecular structures are subsumed under the Formula (I)

wherein $R_1$ is hydrogen, halogen, alkyl, alkoxy, predominantly fluorine-substituted alkoxy, alkanoyl, or carbethoxy; $R_2$ is hydrogen, $C_1$-$C_3$ alkyl, $C_1$-$C_3$ alkoxy, methoxyethoxy, or ethoxyethoxy; $R_3$ is hydrogen, $C_1$-$C_3$ alkyl, $C_2$-$C_5$ fluorinated alkyl, methoxyethyl, methoxypropyl, or ethoxyethyl; and $R_4$ is H, $C_1$-$C_3$ alkyl, $C_2$-$C_5$ fluorinated alkyl, $C_1$-$C_3$ alkoxy, methoxyethoxy, or ethoxyethoxy, are known to exert the pharmacological effect in humans of inhibiting gastric acid secretion.

Among them, pantoprazole—having the systematic chemical name 5-(difluoromethoxy)-2-[[(3,4-dimethoxy-2-pyridinyl)methyl]sulfinyl]-1H-benzimidazole and the molecular Formula (I) wherein $R_1$=5-OCF$_2$H, $R_2$=OCH$_3$, $R_3$=CH$_3$ and $R_4$=H—is a subject of U.S. Pat. No. 4,758,579.

Pantoprazole is the active ingredient of a pharmaceutical product that is marketed in the United States by Wyeth-Ayerst Inc. under the brand name Protonix®. Protonix® is approved by the U.S. Food and Drug Administration for short-term treatment of erosive esophagitis associated with gastroesophageal reflux disease (GERD), maintenance of healing of erosive esophagitis and pathological hypersecretory conditions including Zollinger-Ellison syndrome. According to the package insert for Protonix®, the product contains a monosodium salt of pantoprazole (hereafter "pantoprazole sodium") in a sesquihydrate state of hydration.

Omeprazole—having the systematic chemical name 2-[[(3,5-dimethyl-4-methoxy-2-pyridyl)methyl]sulfinyl]-5-methoxy-1H-benzimidazole and the molecular Formula (I) wherein $R_1$=5-OCH$_3$, $R_2$=CH$_3$, $R_3$=CH$_3$ and $R_4$=CH$_3$—is a subject of U.S. Pat. No. 4,508,905. It is marketed under the brand name Prilosec® by AstraZeneca for treatment of duodenal ulcer, gastric ulcer and GERD; maintenance of healing of erosive esophagitis, and long term treatment of pathological hypersecretory conditions.

Lansoprazole—having the systemic chemical name 2-[[[3-methyl-4-(2,2,2-trifluoroethoxy)-2-pyridyl]methyl]sulfinyl]-1H-benzimidazole and the molecular Formula (I) wherein $R_1$=H, $R_2$=CH$_3$, $R_3$=CH$_2$CF$_3$ and $R_4$=H—is a subject of U.S. Pat. No. 4,628,098. Lansoprazole has utility as a drug similar to pantoprazole and omeprazole. It is marketed under the brand name Prevacid® by TAP Pharmaceutical Products for short-term treatment of duodenal ulcer, H. Pylori eradication to prevent recurrence of duodenal ulcer and maintenance of healed duodenal ulcers.

Rabeprazole—having the systematic chemical name 2-[[[4-(3-methoxypropoxy)-3-methyl-2-pyridinyl]methyl]sulfinyl]-1H-benzimidazole and the molecular Formula (I) wherein $R_1$=H, $R_2$=CH$_3$, $R_3$=CH$_2$CH$_2$CH$_2$OCH$_3$ and $R_4$=H—is a subject of U.S. Pat. No. 5,045,552. It is marketed in the United States under the brand name AcipHex® by Janssen Pharmaceutica Products, L.P. for healing of erosive or ulcerative GERD, maintenance of healing of GERD and treatment of symptomatic GERD.

The preparation of 2-[(pyridinyl)methyl]sulfinyl-substituted benzimidazoles of Formula (I) by oxidation of thioethers of Formula (II)

wherein $R_1$, $R_2$, $R_3$ and $R_4$ are as previously defined with respect to Formula (I) is generally known and is discussed in U.S. Pat. Nos. 4,758,579; 4,508,905, 4,628,098 and 5,045,552.

The '905 patent states that oxidation of thioethers of Formula (II)—wherein $R_1$ is hydrogen, alkyl, halogen, or carbomethoxy; $R_2$ is hydrogen, methyl, methoxy, ethoxy, methoxyethoxy, or ethoxyethoxy; $R_3$ is methyl, ethyl, methoxyethyl, or ethoxyethyl; and $R_4$ is methoxy, ethoxy, methoxyethoxy, or ethoxyethoxy—takes place in the presence of an oxidizing agent selected from the group consisting of nitric acid, hydrogen peroxide, peracids, peresters, ozone, dinitrogentetraoxide, iodosobenzene, N-halosuccinimide, 1-chlorobenzotriazole, t-butylhypochlorite, diazobicyclo-[2, 2,2]-octane bromine complex, sodium metaperiodate, selenium dioxide, manganese dioxide, chromic acid, cericammonium nitrate, bromine, chlorine and sulfuryl chloride. MCPBA (m-chloroperbenzoic acid) was the oxidant used in the examples.

The '098 patent states that for oxidizing thioethers of Formula (II)—wherein $R_1$ is H, methoxy or trifluoromethyl; $R_2$ is H or methyl; $R_3$ is H or methyl; and $R_4$ is a $C_2$-$C_5$ fluorinated alkyl—the oxidizing agent is exemplified by peracid e.g. MCPBA, peracetic acid, trifluoroperacetic acid and permaleic acid, or sodium bromite or sodium hypochlorite or hydrogen peroxide. MCPBA is the oxidant that was used in Example 2 of the '098 patent.

The '552 patent states that the oxidation of thioethers of Formula (II)—wherein $R_1$ is H, halogen, lower alkyl, lower alkoxy, halogenated lower alkyl, lower alkoxycarbonyl, or carboxyl; $R_2$ is H or a lower alkyl group; $R_3$ is a substituted alkoxyalkyl group; and $R_4$ is H—can be carried out according to an ordinary process by the use of an oxidizing agent such as hydrogen peroxide, peracetic acid, MCPBA, sodium hypochlorite or sodium hypobromite. MCPBA is the oxidant used in all of the pertinent examples.

According to a general discussion in the '579 patent, compounds of Formula (I)—wherein $R_1$ is a $C_1$-$C_3$ alkoxyl radical which is completely or predominantly substituted by fluorine, or a chlorodifluoromethoxy radical; $R_2$ is H, a $C_1$-$C_3$ alkoxy radical, or a $C_1$-$C_3$ alkyl radical; $R_3$ is a $C_1$-$C_3$ alkyl radical; and $R_4$ is H, a $C_1$-$C_3$ alkoxy radical, or a $C_1$-$C_3$ alkyl radical—can be made by oxidation of sulfides under conditions known to be suitable for the oxidation of sulfides to sulfoxides. The '579 patent mentions hypohalites and peroxyacids, such as peroxyacetic acid, trifluoroperoxyacetic acid, 3,5-dinitroperoxybenzoic acid, peroxymaleic acid and MCPBA.

According to Example 6 of the '579 patent, 2-[(4,5-dimethoxy-2-pyridyl)methyl sulfinyl]-5-(2,2,2-trifluoroethoxy)-1H-benzimidazole is prepared by dissolving 2-[(4,5-dimethoxy-2-pyridyl)methylthio]-5-(2,2,2-trifluoro ethoxy)-1H-benzimidazole in 15 ml of dioxane and adding 2.5 ml of 1N sodium hydroxide (NaOH) solution. A mixture of 3 ml of 8% strength sodium hypochlorite (NaOCl) solution and 3.5 ml of 1N sodium hydroxide solution is added dropwise over the course of 2 hours while cooling to 0°-5° C. After addition of 5 ml of 5% strength sodium thiosulfate solution, the mixture is concentrated to dryness, the residue is taken up in water and the mixture is brought to pH 7 with phosphate buffer. The solid, which has precipitated out, is filtered off with suction, dried and recrystallized from ethyl acetate/diisopropyl ether. The yield was reported to be 55%.

From a review of the examples of the '579, '905, '098 and '552 patents, MCPBA appears to be a preferred agent for effecting oxidation of thioethers of Formula (II) to sulfoxides of Formula (1). However, MCPBA is prone to cause overoxidation of the thioether group leading to the production of sulfones of Formula (III)

An abundant literature has been generated by the overoxidation problem and numerous mild oxidants have been proposed for effecting the oxidation: WO 99/47514 (perborates), U.S. Pat. No. 5,391,752 (magnesium monoperoxyphthalate); U.S. Pat. No. 6,313,303 (perborate/acid anhydride or metal catalyst or N-halosuccinimide, 1,3-dihalo-5,5-dimethylhydantoin or dichloroisocyanurate); European Patent Publications Nos. 484,265 A (ammonium molybdate) and 302,720 (vanadium oxide); and Spanish Patents Nos. 539,793 (iodosobenzene); 540,147 (methyliodosobenzene) and 550,070 (sodium periodate).

Jozef Drabowicz, Piotr Kielbasinski and Marian MikoLaJczyk, writing before 1988, observed that in the chemical literature at that time that there had been only a single report on the use of an inorganic hypochlorite (NaOCl) for the selective oxidation of sulfides to sulfoxides. Drabowicz, J.; Kielbasinski, P.; MikoLaJczyk, M. "Synthesis of Sulphoxides", Patai, S.; Rappoport, Z.; Stirling, C. *The Syntheses of Sulphones and Sulphoxides*, p. 249 (J. Wiley & Sons: New York 1988).

U.S. Pat. No. 6,423,846 discloses a process for preparing lansoprazole by Mitsunobu reaction of 2-hydroxymethyl-3-methyl-4-(2,2,2-trifluoroethoxy)pyridine and 2-mercaptobenzimidazole followed by oxidation of the resulting thioether. The conditions of oxidation included TEMPO (2,2,6,6-tetramethyl-1-piperidinyloxy) as a catalyst and 2.2 equivalents of NaOCl.

It has now been discovered that when sodium hypochlorite is used as an oxidant for 2-[(pyridinyl)methyl]thio-substituted benzimidazoles under certain controlled conditions, one can obtain the sulfoxide derivative in high yield and with low levels of unreacted starting material or overoxidized side products. Those skilled in the art will immediately appreciate the economic advantages of sodium hypochlorite as an oxidizing agent. It is an inexpensive staple article of commerce. Procedures for safe handling and disposal are well established. Although sodium perborate is less costly and harmful to the environment than MCPBA, its advantages in this regard are less pronounced than those of sodium hypochlorite.

SUMMARY OF THE INVENTION

In one aspect, the present invention provides a process comprising admixing a thioether of Formula (II), wherein $R_1$ is hydrogen, halogen, $C_1$-$C_3$ alkyl, $C_1$-$C_3$ alkoxy, predominantly fluorine-substituted $C_1$-$C_3$ alkoxy, $C_1$-$C_3$ alkanoyl, or carbethoxy; $R_2$ is hydrogen, $C_1$-$C_3$ alkyl, $C_1$-$C_3$ alkoxy, methoxyethoxy, or ethoxyethoxy; $R_3$ is hydrogen, $C_1$-$C_3$ alkyl, $C_2$-$C_5$ fluorinated alkyl, methoxyethyl, methoxypropyl, or ethoxyethyl; and $R_4$ is H, $C_1$-$C_3$ alkyl, $C_2$-$C_5$ fluorinated alkyl, $C_1$-$C_3$ alkoxy, methoxyethyl, or ethoxyethoxy with about 1.05 to about 1.6 molar equivalents of an active chlorine-containing oxidant; and recovering a sulfoxide of Formula (I) wherein $R_1$, $R_2$, $R_3$ and $R_4$ are as previously defined. In preferred embodiments, the R groups are defined such that the recovered sulfoxide is pantoprazole, lansoprazole, omeprazole, or rabeprazole, with pantoprazole being the most preferred. The active chlorine-containing oxidant is preferably N-chlorophthalimide, N-chlorosaccharin, or trichloroisocyanuric acid, and is most preferably sodium hypochlorite.

The admixing step may further comprise preparing a solution or mixture of the thioether in an organic solvent, and adding an active chlorine-containing oxidant such as sodium hypochlorite to the solution or mixture of thioether. The organic solvent is preferably acetonitrile, ethyl acetate, butyl acetate, methyl acetate, or dichloromethane, and is most preferably ethyl acetate or acetonitrile. The admixing step can be performed under basic conditions by adding about 2.5 to about 5.0, preferably about 4 molar equivalents of an alkali metal base such as NaOH. Preferably, the sodium hypochlorite is added by slow addition and is added as a solution or mixture in water. Preferably, the solution or mixture of the thioether is cooled to a reduced temperature of 5° C. or below, most preferably 0° C. or below, before adding the sodium hypochlorite.

The recovering step may further comprise admixing the solution or mixture with sodium metabisulfite ($Na_2S_2O_5$). The recovering may also comprise adjusting the pH of the solution or mixture to about 8 to about 8.5 with an acid, preferably hydrochloric acid. The recovering step may comprise precipitation. The recovering step may further comprise adding an anti-solvent, preferably toluene, hexane, or methyl tertiary butyl ether (MTBE). The recovering step may comprise separating the resulting two phase system.

Especially when the recovered sulfoxide is pantoprazole, the process may further comprise admixing the recovered sulfoxide of Formula (I) with a source of sodium ions in a solvent or solvent mixture to form the sesquihydrate of the sodium salt of the sulfoxide of Formula (I). The present invention provides a process for preparing the sesquihydrate of the sodium salt of the sulfoxide of Formula (I). The process comprises admixing the recovered sulfoxide of Formula (I) with a source of sodium ions in a solvent that is a protic solvent, an aprotic solvent, or a mixture thereof; and recovering the sesquihydrate of the sodium salt of the sulfoxide of Formula (1). Preferably, the protic solvent is water or methanol. Preferably, the aprotic solvent is toluene, ethyl acetate, or acetonitrile. Most preferably, when the protic solvent is methanol, the aprotic solvent is toluene, and when the protic solvent is water, the aprotic solvent is ethyl acetate.

When the polar solvent is water, it is added at a ratio of 3% or less relative to the amount of pantoprazole. Preferably, the sesquihydrate of the sodium salt of the sulfoxide of Formula (I) is pantoprazole sesquihydrate.

The oxidation process and the salification process can be merged by adding the source of sodium ions, such as sodium hydroxide, in the binary solvent mixture to the organic phase obtained at the conclusion of the oxidation process.

The present invention provides a compound of Formula (I) obtained by the process described in detail below containing less than about 0.2% total impurities, more preferably less than about 0.1%, most preferably less than about 0.05% total impurities as percentage area HPLC. The present invention also provides pantoprazole containing less than about 0.2% total impurities, more preferably less than about 0.1%, most preferably less than about 0.05% total impurities as percentage area HPLC. The sesquihydrate of Formula (I) obtained by the process of the present invention is preferably likewise highly purified.

The present invention provides a compound of Formula (I) obtained by the process described in detail below containing less than about 0.2% sulfone, more preferably less than about 0.15% sulfone as percentage area HPLC. The present invention also provides pantoprazole containing less than about 0.2% sulfone, more preferably less than about 0.15% sulfone as percentage area HPLC.

In yet another aspect, the present invention provides for novel chlorinated derivatives of pantoprazole. In one embodiment, the present invention provides a mixture comprising 5-(difluoromethoxy)-2-[[(3,4-dimethoxy-2-pyridinyl)-chloromethyl]sulfinyl]-1H-benzimidazole in an amount of about 0.1% or greater. In another embodiment, the present invention provides isolated 5-(difluoromethoxy)-2-[[(3,4-dimethoxy-2-pyridinyl)-chloromethyl]sulfinyl]-1H-benzimidazole. In yet another embodiment, the present invention provides 5-(difluoromethoxy)-2-[[(3,4-dimethoxy-2-pyridinyl)-chlorohydroxymethyl]sulfinyl]-1H-benzimidazole.

In another aspect, the present invention provides a process comprising admixing 5-(difluoromethoxy)-2-[[(3,4-dimethoxy-2-pyridinyl) methyl]thio]-1H-benzimidazole with a quantity of an active chlorine-containing oxidant such as NaOCl of about 3 to about 5, preferably about 1.5 to about 2.5 molar equivalents and a quantity of an alkali metal base such as NaOH of about 1.5 to about 2.5 molar equivalents in a water miscible protic solvent or a water miscible aprotic solvent at ambient or elevated temperature, and recovering a 2-[chloro-(pyridinyl)methyl]sulfinyl substituted benzimidazole. In preferred embodiments, the substituted benzimidazole is 5-(difluoromethoxy)-2-[[(3,4-dimethoxy-2-pyridinyl)-chloromethyl]sulfinyl]-1H-benzimidazole or 5-(difluoromethoxy)-2-[[(3,4-dimethoxy-2-pyridinyl)-chlorohydroxymethyl]sulfinyl]-1H-benzimidazole. The recovering step may further comprise admixing the solution or mixture with sodium metabisulfite and adjusting the pH to about 8.5.

In another aspect, the present invention provides a method of quantifying the amount of a compound that is 5-(difluoromethoxy)-2-[[(3,4-dimethoxy-2-pyridinyl)-chloromethyl] sulfinyl]-1H-benzimidazole or 5-(difluoromethoxy)-2-[[(3,4-dimethoxy-2-pyridinyl)-chlorohydroxymethyl]sulfinyl]-1H-benzimidazole in a mixture comprising the compound and pantoprazole. The method comprises chromatographing a sample of the mixture to obtain a value proportionate to the amount of the compound in the mixture, chromatographing a solution of known concentration of the compound to obtain a value proportionate to the amount of the compound in the solution, and determining the quantity of the compound in the mixture by comparing the proportionate value obtained from the sample with the proportionate value obtained from the solution of known concentration. In one embodiment, the value proportionate to the amount of the compound in the mixture and in the solution is the area under the peak corresponding to the compound in a chromatogram resulting from chromatographing the sample and the solution, respectively. Preferably, the values proportionate to the amount of compound in the mixture and the solution are determined by electronic integration of the areas under the peaks corresponding to the compound in the chromatograms. In another embodiment, the value proportionate to the amount of the compound in the mixture and in the solution is the height of the peak corresponding to the compound in a chromatogram resulting from chromatographing the sample and the solution, respectively.

In yet another aspect, the present invention provides a method of identifying a compound other than pantoprazole in a mixture containing pantoprazole and at least one compound other than pantoprazole. The method comprises chromatographing a sample of the mixture under pre-determined chromatographic conditions to associate the compound with a position, comparing the position of the compound to the position of a reference marker that is 5-(difluoromethoxy)-2-[[(3,4-dimethoxy-2-pyridinyl)-chloromethyl]sulfinyl]-1H-benzimidazole or 5-(difluoromethoxy)-2-[[(3,4-dimethoxy-2-pyridinyl)-chlorohydroxymethyl]sulfinyl]-1H-benzimidazole determined by chromatographing the reference marker under the same or substantially the same chromatographic conditions as the sample, and identifying the compound from its position relative to the position of the reference marker.

In a preferred embodiment, the chromatographing is performed on an apparatus comprising an injector, a detector, a generally tubular column containing an adsorbent and having a first open end in fluid communication with the injector and a second open end in fluid communication with the detector, and a recording device. In this embodiment, chromatographing comprises injecting the sample into a stream of an eluent by means of the injector, carrying the sample in the eluent stream to the adsorbent at the first end of the column, partitioning the compound contained in the sample between the adsorbent and the eluent as it traverses the column in the eluent stream, eluting the compound from the second end of the column and carrying the compound through the detector in the eluent stream, transmitting a signal from the detector to the recording device in response to passage of the compound through the detector, and recording by means of the recording device the position of the compound. The eluent may be a gas or a liquid.

The recording step may further comprise recording the position of the compound by a deflection in a chromatogram produced on the recording device or a number substantially corresponding to the period of time between injection and passage of the compound through the detector in units of time.

The comparing step may further comprise calculating a relative retention time of the compound by dividing the period of time between injection of the sample and passage of the compound through the detector by the increment of time between injection of the reference marker and passage of the reference marker through the detector. In this embodiment, identifying the compound comprises matching the relative retention time of the compound to a pre-determined relative retention time of a known compound and using the match to identify the compound as the known compound.

In another embodiment, chromatographing is performed using an assembly comprising a plate having a generally planar surface bounded by first and second edges and an adsorbent distributed substantially uniformly over the surface, and a vessel sized to receive and orient the plate substantially vertically with the first edge down and the second edge up. Chromatographing comprises applying the sample to the surface of the plate at a location proximate to the first edge, placing a quantity of an eluent in the vessel, placing the plate in the vessel with the first edge oriented down and admixing the eluent and the second edge oriented up, allowing the eluent to rise up the surface of the plate by capillary interaction with the adsorbent to a level proximate to the second edge of the plate, whereupon the compound traverses a distance $d_1$ from the location where the sample was applied to a second location, removing the plate from the vessel to stop the rise of the eluent, noting distance $d_2$ between the location where the sample was applied and the level to which the eluent rose and assigning to the compound a position corresponding to a number, $R_f$, obtained by dividing $d_1$ by $d_2$.

DETAILED DESCRIPTION OF THE PREFERRED EMBODIMENTS

In a first aspect, the present invention provides an oxidation process that is useful for preparing 2-[(pyridinyl)methyl] sulfinyl-substituted benzimidazoles of Formula (I)

wherein $R_1$ is hydrogen, halogen, $C_1$-$C_3$ alkyl, $C_1$-$C_3$ alkoxy, predominantly fluorine-substituted $C_1$-$C_3$ alkoxy, $C_1$-$C_3$ alkanoyl, or carbethoxy; $R_2$ is hydrogen, $C_1$-$C_3$ alkyl, $C_1$-$C_3$ alkoxy, methoxyethoxy, or ethoxyethoxy; $R_3$ is hydrogen, $C_1$-$C_3$ alkyl, $C_2$-$C_5$ fluorinated alkyl, methoxyethyl, methoxypropyl, or ethoxyethyl; and 4 is H, $C_1$-$C_3$ alkyl, $C_2$-$C_5$ fluorinated alkyl, $C_1$-$C_3$ alkoxy, methoxyethoxy, or ethoxyethoxy by admixing a thioether of Formula (II):

wherein $R_1$, $R_2$, $R_3$ and $R_4$ are as previously defined, with an active chlorine-containing oxidant.

Preferred sulfoxides of Formula (I) are those wherein $R_1$ is H, $OCH_3$, $-OCF_2H$, or $OCH_2CF_3$; $R_2$ is H, methyl methoxy, or ethoxy; $R_3$ is methyl, $-CH_2CF_3$, or $-CH_2CH_2CH_2OCH_3$; and $R_4$ is H or $CH_3$.

Especially preferred sulfoxides of Formula (I) are pantoprazole, omeprazole, lansoprazole and rabeprazole, with pantoprazole being the most preferred.

The sulfur atom of sulfoxides of Formula (I) is a chiral center, making compounds of Formula (I) chiral compounds. The process of the present invention is applicable to individual stereoisomers and to racemic and non-racemic mixtures of stereoisomers. Although we have chosen to represent the sulfoxide moiety by the convention (C→O), there are other conventions for representing the same moiety, namely S=O and $S^+$—$O^-$. The different conventions are understood by those skilled in the art to represent the same substances.

In accordance with the oxidation process of the present invention, a thioether of Formula (II) is admixed with about 1.05 to about 1.6 molar equivalents of an active chlorine-containing oxidant.

Sodium hypochlorite is the preferred active chlorine-containing oxidant. Other active chlorine-containing oxidants that can be substituted for NaOCl include, but are not limited to N-chlorophthalimide, N-chlorosaccharin, and trichlorisocyanuric acid.

According to preferred embodiments of the oxidation process of the invention, the thioether is admixed with about 1.05 to about 1.6 molar equivalents of NaOCl. The NaOCl is preferably provided as an aqueous solution or mixture, yet more preferably a solution or mixture with an activity (i.e. weight percent) of about 9.4 to about 13%, although the activity is not critical to practice of the invention.

The thioether is admixed with the NaOCl under basic conditions. The basic conditions can be established by preparing a solution or mixture of the thioether in an organic solvent and then adding an alkali metal base to the solution or mixture, either as an aqueous or alcoholic solution or mixture or in solid form. The alkali metal base can be an alkali metal hydroxide, alkoxide, or hydride. Preferred alkali metals are sodium and potassium, with sodium being most preferred. Exemplary alkali metal bases are sodium hydroxide, potassium hydroxide, lithium hydroxide, sodium methoxide, lithium methoxide, sodium ethoxide, lithium ethoxide, potassium t-butoxide, and sodium hydride. Most preferably the alkali metal base is NaOH. Sodium hydroxide is used in an amount of about 2.5 to about 5.0 molar equivalents with respect to the thioether, more preferably about 4 molar equivalents.

In one embodiment, the amount of NaOCl is about 1.2 to about 1.6 molar equivalents, and the amount of NaOH is about 2.5 to about 5.0 molar equivalents. In other embodiments, the amount of NaOCl can be 1.3 to 1.5 molar equivalents. The amount of NaOH can be 3.5 to 4 molar equivalents.

Preferred organic solvents include acetonitrile, ethyl acetate, isobutyl acetate, butyl acetate, methyl acetate, and dichloromethane. Acetonitrile is especially preferred because the product purity is generally especially high when that solvent is used. Ethyl acetate is another preferred solvent for a different reason (although it too yields the product in high yield and purity).

The resulting mixture of the solution or mixture of sulfoxide of Formula (II) in the organic solvent and the active chlorine containing oxidant, may be either a homogeneous mixture or a mixture of two liquid phases. Sulfoxide products of Formula (I) tend to crystallize in high yield from acetonitrile, which is parlayed into a simple and efficient recovery method in the process of the present invention. When the organic solvent is either isobutyl acetate or about 2 to about 10 volumes of acetonitrile, and sodium metabisulfite ($Na_2S_2O_5$) is added to the reaction mixture, the sulfoxide product can be recovered by simply allowing it to stand until crystallization is satisfactorily complete. When the reaction mixture comprises two phases, there is no need for phase separation. Then, the rest of the reaction mixture can be separated conventionally, for example, by such techniques as filtration, vacuum filtration, centrifugation, and decantation. In this embodiment, the process may further comprise adding an acid to the reaction mixture.

The process may also further comprise adding an anti-solvent. The anti-solvent is preferably toluene, hexane, or methyl tertiary butyl ether (MTBE). As used herein, the term "anti-solvent" refers to a liquid that when added to a solution of X in the solvent, induces crystallization or precipitation of X. Precipitation of X is induced by the anti-solvent when addition of the anti-solvent causes X to precipitate from the solution more rapidly or to a greater extent than X precipitates from a solution containing an equal concentration of X in the same solvent when the solution is maintained under the same conditions for the same period of time but without adding the anti-solvent. Precipitation or crystallization can be perceived visually as a clouding of the solution or formation of distinct particles of X suspended in the solution or collected at the bottom the vessel containing the solution.

When the organic solvent is selected from the group consisting of ethyl acetate, butyl acetate, methyl acetate, dichloromethane and more than 10 volumes of acetonitrile, sodium metabisulfite ($Na_2S_2O_5$) is added to the reaction mixture and a two phase systems is obtained. The phases are separated and the compound of Formula (I) is recovered from the organic phase. Preferably, the compound of Formula (I) is pantoprazole sodium. The compound of Formula (I) may be recovered by evaporating the organic solvent, adding an apolar solvent such as methyl-t-butyl ether, and filtering the mixture. The compound of Formula (I) may also be recovered by concentrating the organic phase.

Preferably, the active chlorine-containing oxidant is added to the mixture slowly, e.g. at a constant flow rate over a period of about 15 minutes to about 6 hours, or more.

To minimize formation of sulfones of Formula (III), the slow addition is conducted at reduced temperature. It is sufficient to cool only the thioether solution or mixture, although the active chlorine-containing oxidant solution or mixture also may be cooled. A reduced temperature of about 5° C. or below, more preferably about 0° C. or below is preferably maintained throughout the course of addition of the active chlorine-containing oxidant.

After addition of the active chlorine-containing oxidant is complete, the reaction mixture may be maintained at reduced temperature or be allowed to warm to ambient temperature until the oxidation is satisfactorily complete. The extent of completion of the reaction may be monitored by conventional means such as thin layer chromatography or high performance liquid chromatography, or by any suitable spectroscopic method performed on aliquots of the reaction mixture.

The inventive process produces compounds of Formula (I) in high yield and essentially free of overoxidation products.

We have further discovered preferred procedures for recovering sulfoxides of Formula (I) from the oxidation reaction mixture in high yield and high purity.

According to one such procedure, any excess unreacted active chlorine-containing oxidant is quenched by admixing the reaction mixture with sodium metabisulfite ($Na_2S_2O_5$), which is preferably provided as an aqueous solution. Typically the quenched reaction mixture will be basic. Its pH should be adjusted to about 8 to about 8.5, which is preferably done by adding aqueous hydrochloric acid (HCl) to the reaction mixture.

According to an alternative procedure, the unreacted active chlorine-containing oxidant is quenched by admixing the reaction mixture with sodium thiosulfate ($Na_2S_2O_3$), also preferably provided as an aqueous solution. When sodium thiosulfate is used, the pH is preferably adjusted to within the same 8.0-8.5 pH range with ammonium sulfate or ammonium chloride.

If there are two phases at this point in the preferred recovery procedure, they can be separated. At pH 8-8.5, sulfoxides of Formula (I) partition predominantly in the water-immiscible organic phase from where they can be recovered. The aqueous phase can be extracted with any water-immiscible organic solvent to increase recovery of the product and the extracts can be combined with the organic phase. Optionally, the organic phases can be washed and dried using conventional methods. The solutions may be allowed to stand at ambient or reduced temperature to induce crystallization directly from the solution or the solution can be concentrated and the residue subjected to chromatography to further purify the sulfoxide product.

The compound of Formula (I) obtained by the process provided in the present invention preferably contains less than about 0.2% total impurities, more preferably less than about 0.1%, most preferably less than about 0.05% total impurities as percentage area HPLC.

In another aspect, the present invention provides pantoprazole containing less than about 0.2% total impurities, more preferably less than about 0.1%, most preferably less than about 0.05% total impurities as percentage area HPLC.

The compound of Formula (I) obtained by the process provided in the present invention preferably contains less than about 0.2% sulfone, more preferably less than about 0.15% sulfone as percentage area HPLC.

In another aspect, the present invention provides pantoprazole containing less than about 0.2% sulfone, more preferably less than about 0.15% sulfone as percentage area HPLC.

The present invention further provides a process for preparing the sesquihydrate of the sodium salt of the sulfoxide of Formula (I). This process comprises admixing the sulfoxide of Formula (I) with a source of sodium ions in a solvent selected from the group consisting of: a protic solvent, an aprotic solvent, and mixtures thereof, and recovering the sesquihydrate of the sodium salt of the sulfoxide of Formula (I). Preferably, the protic solvent is selected from the group consisting of MeOH and water. Preferably, the aprotic solvent is selected from the group consisting of toluene, ethyl acetate, or acetonitrile. Most preferably, when the protic solvent is MeOH, the aprotic solvent is toluene, and when the protic solvent is water, the aprotic solvent is ethyl acetate. The admixing step is preferably performed with stirring.

When the polar solvent is water, it is added at a ratio of 3% or less relative to the amount of pantoprazole. Preferably, the sesquihydrate of the sodium salt of the sulfoxide of Formula (I) is pantoprazole sesquihydrate.

Preferably, the compound of formula (I) is obtained by the oxidation process described above, and is highly purified. The sesquihydrate prepared by using this compound of formula (I) is also highly purified, and contains less than about 0.2% total impurities, preferably less than about 0.1% total impurities, most preferably less than about 0.05% total impurities as percentage area HPLC.

In another aspect, the present invention provides pantoprazole sesquihydrate containing less than about 0.2% total impurities, more preferably less than about 0.1%, most preferably less than about 0.05% total impurities as percentage area HPLC.

It will be appreciated by those in the art that the oxidation process and the salification process can be merged by adding the source of sodium ions, like sodium hydroxide, in the binary solvent mixture to the organic phase obtained at the conclusion of the oxidation process.

In another aspect, the present invention provides novel chlorinated derivatives of pantoprazole. One such derivative is 5-(difluoromethoxy)-2-[[(3,4-dimethoxy-2-pyridinyl)-chloromethyl]sulfinyl]-1H-benzimidazole IV. The structure of compound IV was deduced with the aid of $^1$H, $^{13}$C, and DEPT NMR spectroscopy and FAB mass spectrometry. The parent ion at 418.031 au (M+H) is consistent with the assigned structure. The structural formulae below show the proton and carbon chemical shift (δ) in parts per million of compound IV in deuteroacetonitrile referenced to tetramethylsilane internal standard ($\delta_{TMS}$=0.0 ppm).

Figure 1:
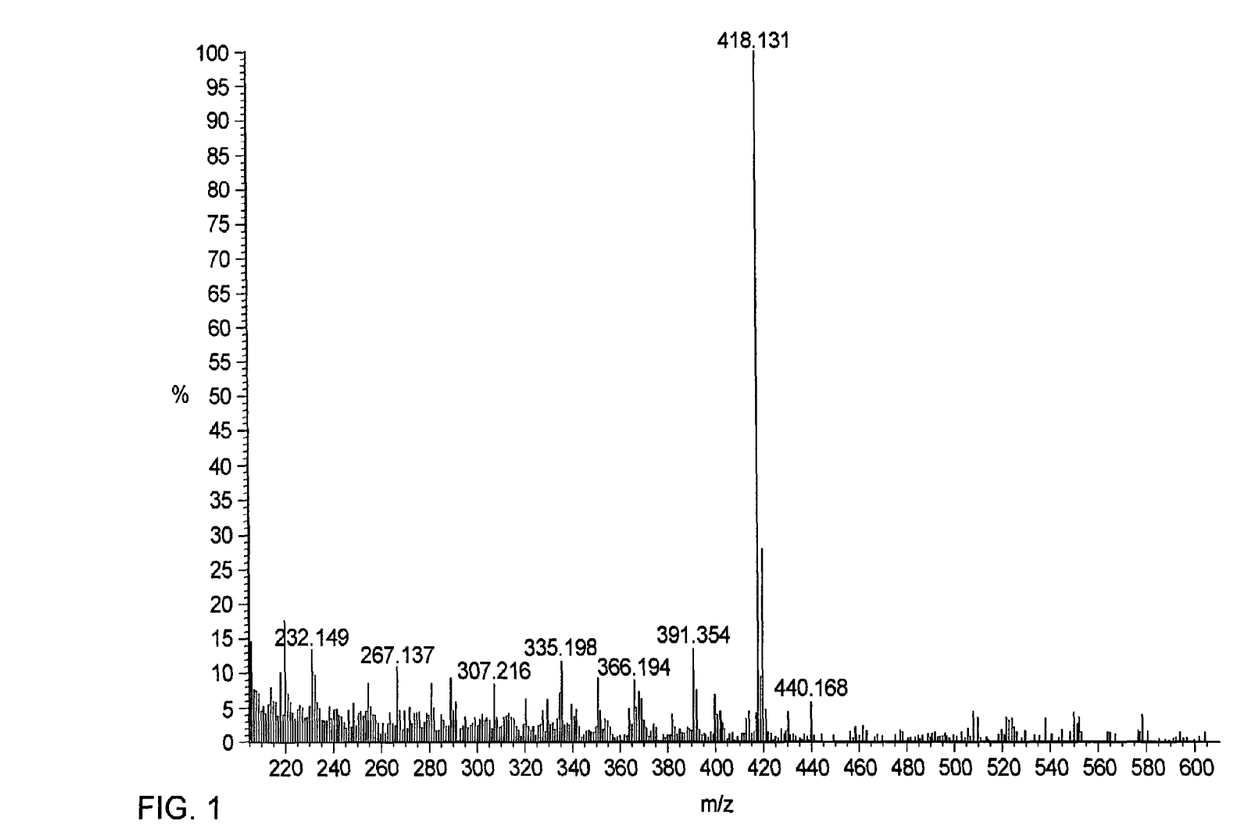
FIG. 1 is a fast atom bombardment ionization (FAB) mass spectrum of 5-(difluoromethoxy)-2-[[(3,4-dimethoxy-2-pyridinyl)-chloromethyl]sulfinyl]-1H-benzimidazole IV. As can be seen, the ratio of the M+H and M+H+2 isotope peak is consistent with a mono-chlorinated compound of molecular mass 417.131 au.
Figure 2:
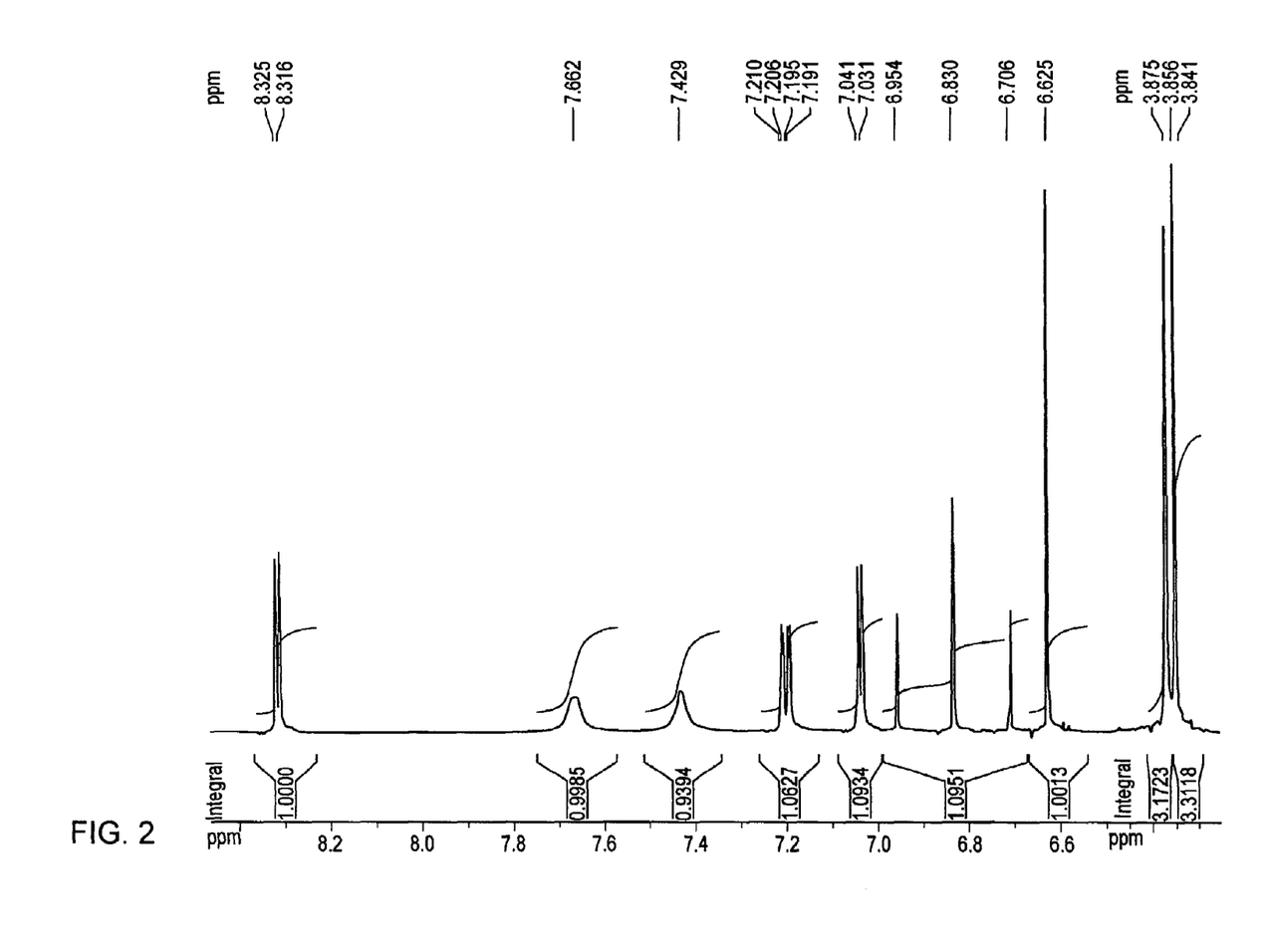
FIG. 2 is a portion of an $^1$H NMR spectrum in deuteroacetonitrile referenced to tetramethylsilane (TMS) containing all hydrogen resonances of compound IV.
Figure 3:
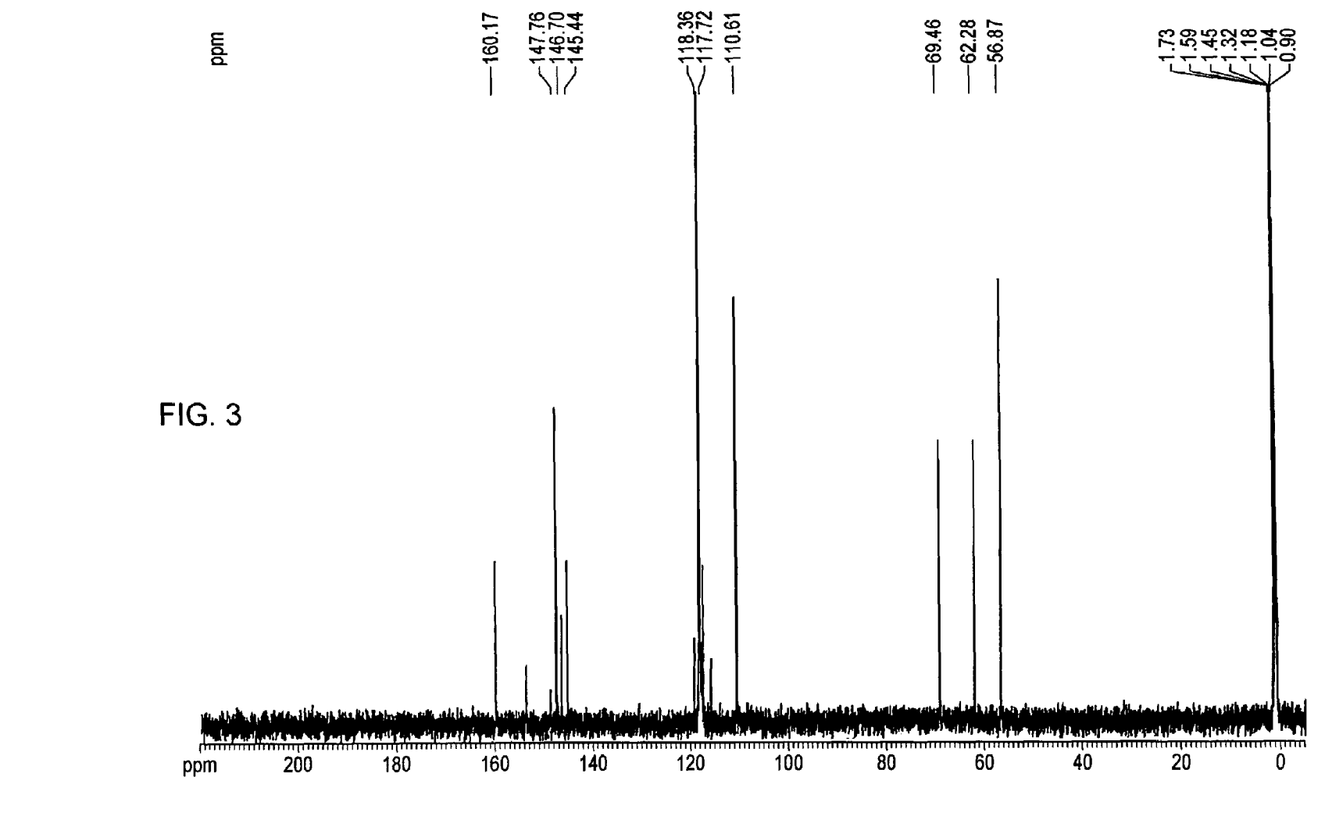
FIG. 3 is a $^{13}$C NMR spectrum in deuteroacetonitrile of compound IV referenced to TMS.

The chemical shifts were extracted from line listings generated with the acquisition of the NMR spectra depicted in FIGS. 2 and 3.

Figure 4:
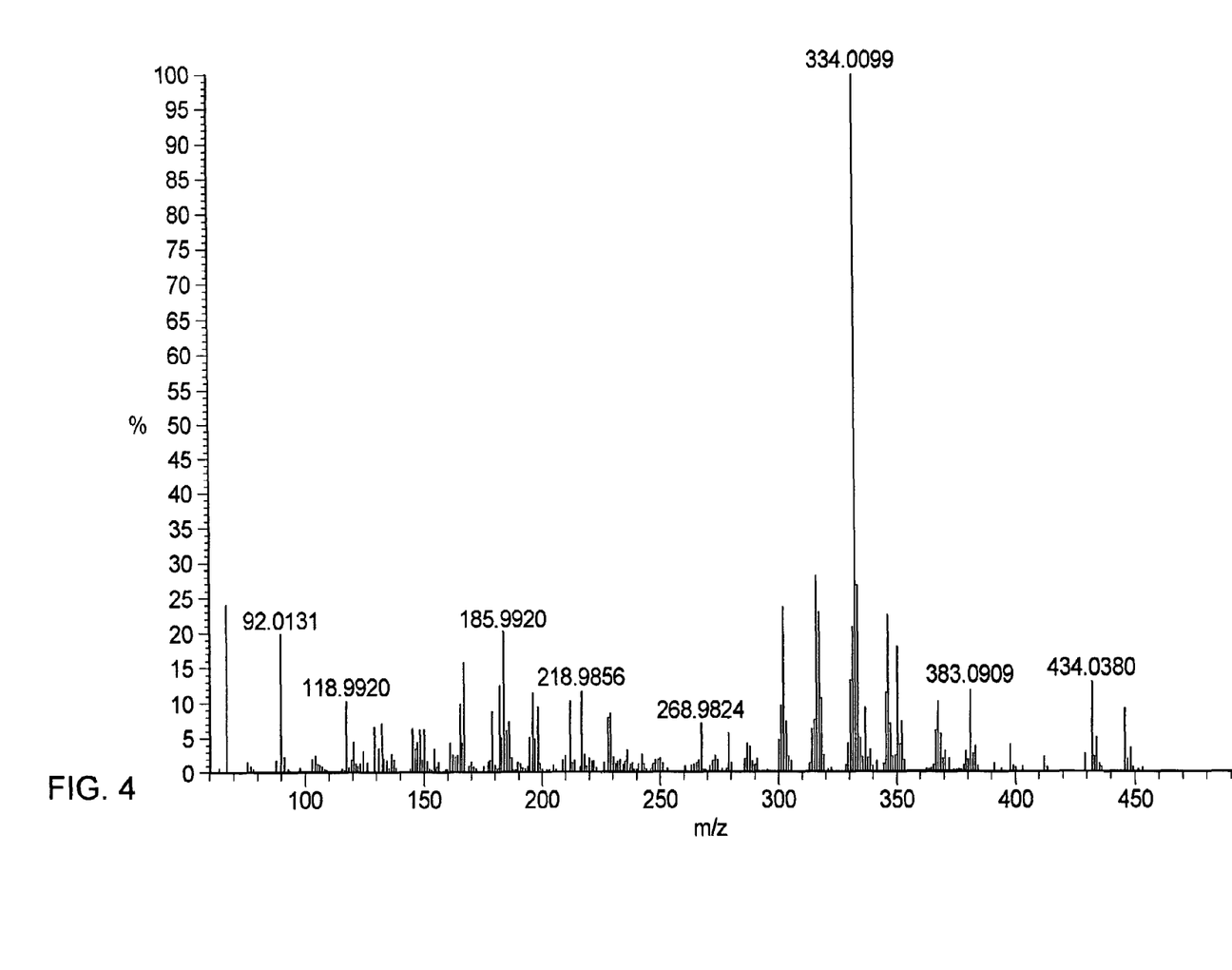
FIG. 4 is a FAB mass spectrum of 5-(difluoromethoxy)-2-[[(3,4-dimethoxy-2-pyridinyl)-chlorohydroxymethyl]sulfinyl]-1H-benzimidazole V. The ratio of the M+H and M+H+2 isotope peak is consistent with a mono-chlorinated compound of molecular mass 433.038 au.
Figure 5:
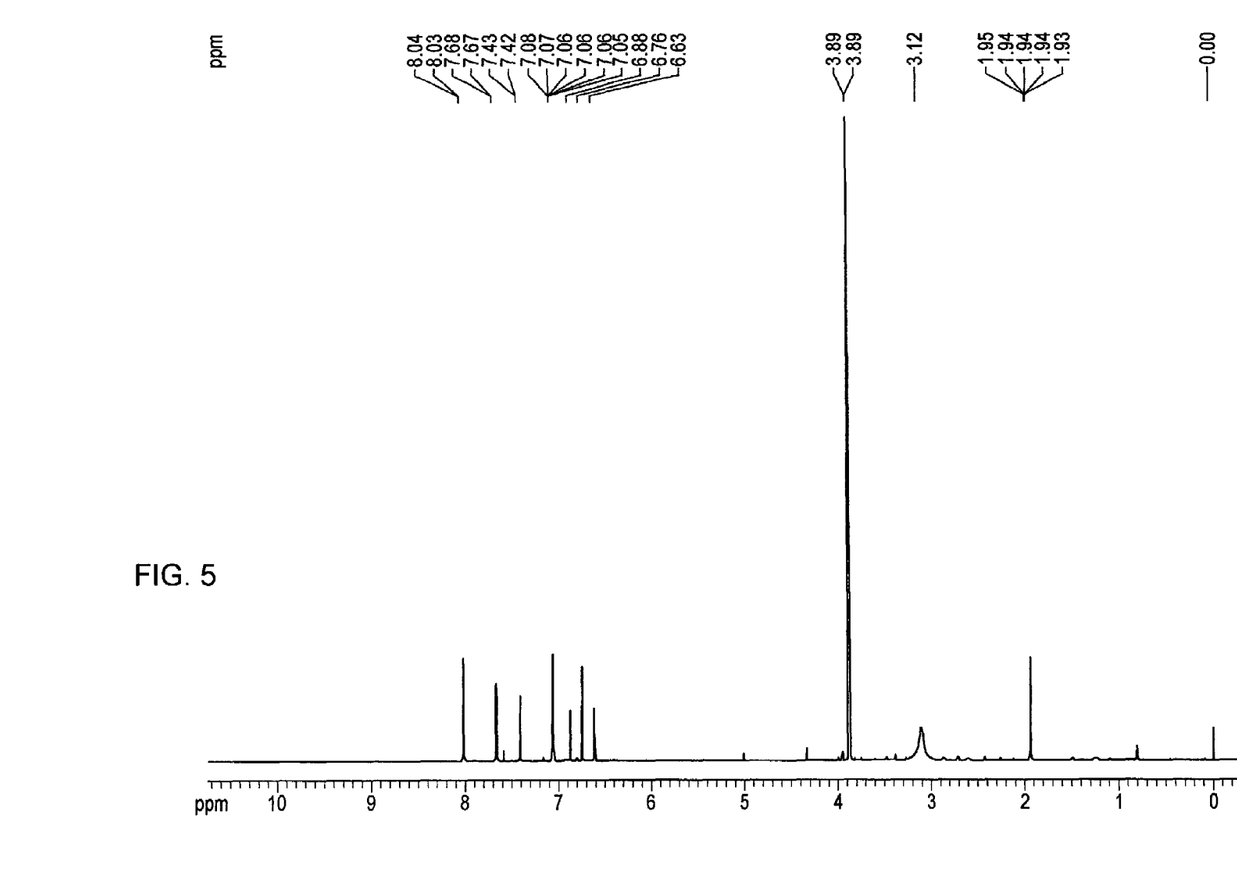
FIG. 5 is an $^1$H NMR spectrum of compound V in deuteroacetonitrile referenced to TMS.
Figure 6:
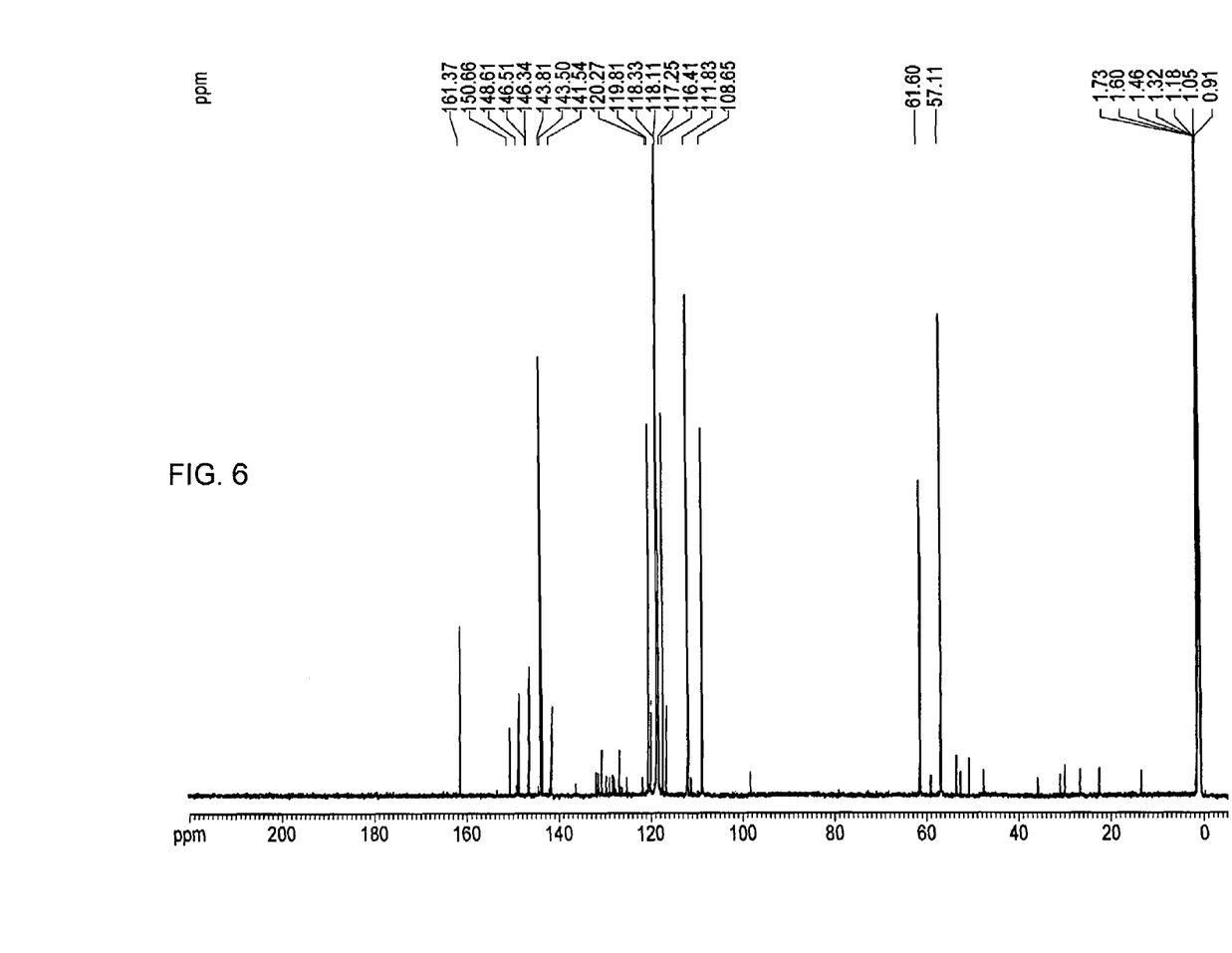
FIG. 6 is a $^{13}$C NMR spectrum of compound V in deuteroacetonitrile referenced to TMS.
Figure 7:
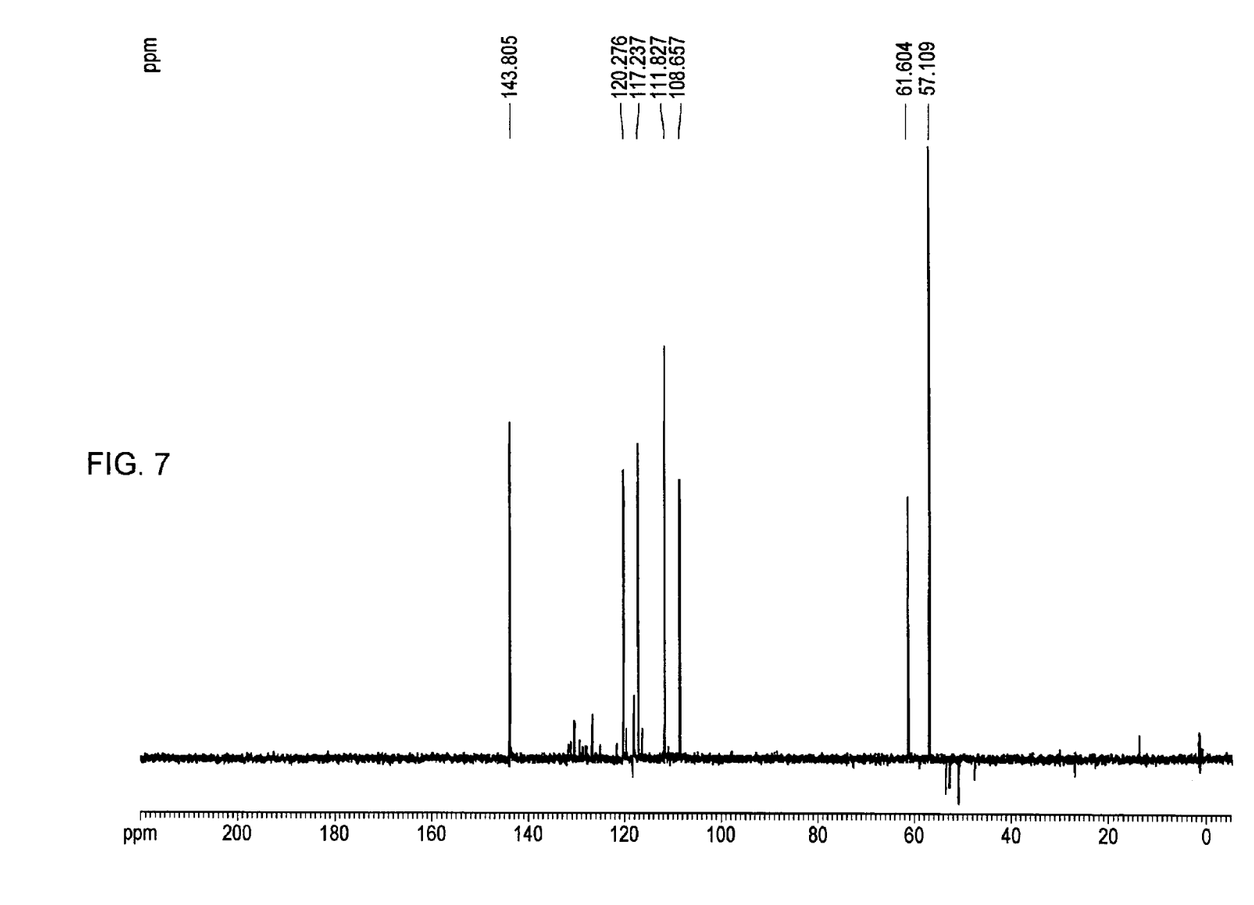
FIG. 7 is a spectrum result of a DEPT NMR (Distortionless Enhancement by Polarization Transfer) experiment that shows that methylene groups are not present in compound V.

The second chlorinated pantoprazole derivative is 5-(difluoromethoxy)-2-[[(3,4-dimethoxy-2-pyridinyl)-chlorohydroxymethyl]sulfinyl]-1H-benzimidazole V. Compound V has been characterized by $^1$H and $^{13}$C NMR spectroscopy and FAB mass spectrometry. The parent ion at 434.0380 au (M+H) is consistent with the assigned structure. The structural formulae below show the proton and carbon chemical shift (δ) in parts per million of compound V in deuteroacetonitrile referenced to tetramethylsilane internal standard ($\delta_{TMS}$=0.0 ppm)

The chemical shifts were extracted from line listings generated with the acquisition of the NMR spectra depicted in FIGS. 5 and 6.

Chlorinated pantoprazole derivatives IV and V can be produced by reaction of 5-(difluoromethoxy)-2-[[(3,4-dimethoxy-2-pyridinyl) methyl]thio]-1H-benzimidazole with NaOH and about 3 to about 5 molar equivalents of NaOCl under conditions especially developed to produce these derivatives. Those conditions include admixing 5-(difluoromethoxy)-2-[[(3,4-dimethoxy-2-pyridinyl) methyl]thio]-1H-benzimidazole compound VI with a quantity of NaOCl of about 3 to about 5, preferably about 1.5 to about 2.5 molar equivalents and a quantity of NaOH of about 1.5 to about 2.5 molar equivalents. Preferred relative quantities of these reagents are about 1.8 molar equivalents of each with respect to benzimidazole VI. Compound VI, NaOCl and NaOH are admixed in a water miscible protic solvent, such as methanol, ethanol and i-propanol, or water miscible aprotic solvent such as acetonitrile and tetrahydrofuran. The reaction is conducted at ambient or elevated temperature, preferably ambient temperature. In all other respects, the reaction conditions can be the same as those of the process previously described for oxidizing 2-[(pyridinyl)methyl]thio-substituted benzimidazoles selectively to 2-[(pyridinyl)methyl] sulfinyl-substituted benzimidazoles. After completing the reaction, the mixture is treated with aqueous sodium metabisulfite to pH 8.5 and stirred at room temperature for 1 hour. The two phases from the resulting reaction are separated, and the solvent is evaporated with vacuum. Isolation of compounds IV and V can be performed by chromatography. Compounds IV and V will be produced in mixture with pantoprazole. In fact, pantoprazole may be the major product.

In general, compounds IV and V can be separated from non-volatile organic components of the reaction mixture, including pantoprazole, and from each other by chromatography over silica gel eluting with ethyl acetate. Other eluents can be used as well, and alumina also is a good adsorbent. While elution of silica gel with ethyl acetate is effective and preferred, it is considered that other adsorbent/eluent combinations can be found that will separate these compounds IV and V from each other and from pantoprazole using routine skill and without undue experimentation Although yields of compounds IV and V are not particularly high, the preparation and isolation of these compounds enabled by this invention is important because of their usefulness for preparing pharmaceutical compositions of pantoprazole (not to mention that the major side product pantoprazole is useful as well). As is apparent from preceding portions of this disclosure, known methods of preparing the active pharmaceutical ingredient pantoprazole produce overoxidized side products. The U.S. Food and Drug Administration's Center for Drug Evaluation and Research (CDER) has promulgated guidelines recommending that new drug and generic drug applicants identify organic impurities of 0.1% or greater in the active ingredient. "Guideline on Impurities in New Drug Substances" 61 Fed. Reg. 371 (1996), "Guidance for Industry ANDAs: Impurities in Drug Substances" 64 Fed. Reg. 67917 (1999). Unless an impurity is a human metabolite, has been tested for safety, or was present in a composition that was shown to be safe in clinical trials, the CDER further recommends that the drug applicant reduce the amount of the impurity in the active ingredient to below 0.1%. Therefore, it is desirable to separate the overoxidized sulfone derivative of pantoprazole, along with other impurities, before pantoprazole prepared by known processes is used in a pharmaceutical product for administration to humans.

There are general techniques whereby the purity of pantoprazole can be improved, such as recrystallization and chromatography. The present invention is not concerned with the particulars of those techniques. Purity can be measured by analytical methods such as gas chromatography (GC), high performance liquid chromatography (HPLC), and thin layer chromatography (TLC). Gas chromatographs; HPLC injectors, tubing, pumps and detectors; recorders, integrators and the like, as well as TLC plates, developing jars and stains are in widespread use today. The operation of all of this standard laboratory equipment is well known to those skilled in the art.

In routine purity testing, the identities of impurities have been pre-determined and the impurities have been associated with a peak position in the chromatogram (or a spot on a TLC plate). Thereafter, the impurity can be identified by its position in the chromatogram, which is conventionally measured in minutes between injection of the sample on the column and elution of the particular component through the detector, known as the "retention time." This time period varies daily based upon the condition of the instrumentation and many other factors. To mitigate the effect that such variations have upon accurate identification of an impurity, practitioners sometimes use "relative retention time" (RRT) to identify an impurity based on the position of its peak in a chromatogram. The RRT of an impurity is its retention time divided by the retention time of some reference marker compound. Thus, a reference marker is useful for qualitative analysis of the components of a mixture.

More detailed discussions of the use of reference markers can be found in Strobel, H. A.; Heineman, W. R., *Chemical Instrumentation: A Systematic Approach*, 3rd ed. (Wiley & Sons: New York 1989) and Snyder, L. R.; Kirkland, J. J. *Introduction to Modern Liquid Chromatography*, 2nd e.d (John Wiley & Sons: New York 1979).

Using the HPLC conditions described in the Examples, compound IV and compound V elute near enough to the analyte of greatest interest, pantoprazole, that they will be found near the center of the chromatogram in essentially any appropriate reverse-phase HPLC method. This is advantageous because impurity identification is most accurate when the RRT values are neither extremely high nor extremely low. The RRT values of compounds IV and V make them well suited as reference markers in purity analysis of pantoprazole during its processing into a pharmaceutical product.

5-(Difluoromethoxy)-2-[[(3,4-dimethoxy-2-pyridinyl)-chlorohydroxymethyl]sulfinyl]-1H-benzimidazole V is a novel compound. Having never been prepared or isolated before, it constitutes an aspect of this invention in any environment or degree of purity.

5-(Difluoromethoxy)-2-[[(3,4-dimethoxy-2-pyridinyl)-chloromethyl]sulfinyl]-1H-benzimidazole IV has never been produced as a target of organic synthesis or isolated before. However, it has been detected as a minor component (0.05%) in Protonix® by HPLC-MS analysis of an aqueous extract of pulverized Protonix® delayed-release tablets. Thus, an aspect of the present invention provides mixtures of 5-(difluoromethoxy)-2-[[(3,4-dimethoxy-2-pyridinyl)-chloromethyl]sulfinyl]-1H-benzimidazole IV and pantoprazole, such as mixtures containing 1%, 5%, 10%, 20%, 30%, 40%, 50%, 60%, 70%, 80%, 90%, 95%, 99% or 99.9% benzimidazole IV. Yet another aspect of the invention is isolated 5-(difluoromethoxy)-2-[[(3,4-dimethoxy-2-pyridinyl)-chloromethyl] sulfinyl]-1H-benzimidazole IV in any environment.

Compounds IV and V are able to form salts and such salts are within the scope of the compounds of this invention, as are the various gaseous, liquid or solid phases in which they exist. In fact, substances that can be described as having the formulas depicted above in conjunction with the chemical shift assignments are considered within the literal scope of the invention absent at a minimum some covalent modification. However, covalent modification also may produce a product that is within the spirit and scope of the invention as to be equivalent to the compounds explicitly depicted in this disclosure. For instance, such covalent modifications include adding a hydroxy or amine protecting group to compound V or derivatizing the hydroxy group, e.g. to a sulfonate, to make it a better leaving group.

Having thus described the present invention with reference to certain preferred embodiments, the processes for producing sulfoxides of Formula (I), pantoprazole sodium sesquihydrate, and the chlorinated pantoprazole derivatives of the present invention are further illustrated by the non-limiting examples that follow.

EXAMPLES

All NaOH, HCl, NaOCl, and $Na_2S_2O_5$ solutions were aqueous unless otherwise indicated. Where concentration is not otherwise indicated, solutions were saturated.

The composition of the product was monitored by gradient elution, reverse phase high performance liquid chromatography employing the following chromatographic conditions:

Column: RP C-8, 3.5µ, 150×4.6 mm
Mobile Phases:
   A: 10 mM di-ammonium hydrogenphosphate adjusted to pH=7.5 with $H_3PO_4$
   B: 80:20 Acetonitrile:Methanol
Flow rate: 1 ml $min^{-1}$
Detection: UV, λ=285 nm
Column Temp.: 30° C.

| Gradient Program | | |
|---|---|---|
| Time (min.) | A(%) | B(%) |
| 0 | 86 | 14 |
| 10 | 86 | 14 |
| 35 | 42 | 58 |

Karl Fischer analysis was performed using a Metrom 701 KF Titrino using Hydranal Composit 5K reagent.

Preparation of Pantoprazole

Example 1

A flask equipped with a stirrer is charged with ethyl acetate (140 ml). Under mixing, 5-(difluoromethoxy)-2-[[(3,4-dimethoxy-2-pyridinyl) methyl]thio]-1H-benzimidazole VI (5 g, 13.6 mmol) is added to the flask followed by 18.8% aq. NaOH (11.5 ml, d=1.16 g $ml^{-1}$, 4.9 eq.). The reactor is cooled to −10° C. 9.7% NaOCl (9.7 ml, d=1.16 g $ml^{-1}$, 1.04 eq.) is added dropwise over 15 min. The two-phase mixture is stirred at room temperature for 3 h. The phases are then separated, and 27% aq. sodium metabisulfite ($Na_2S_2O_5$) (7 ml) is added to the aqueous phase to quench unreacted oxidant. The organic phase is washed with water, and the aqueous phase is washed twice with ethyl acetate. The organic phases are combined, dried over sodium sulfate ($Na_2SO_4$), and evaporated under 20 mm Hg vacuum. The resulting oil is triturated with methyl t-butyl ether and filtered to obtain pantoprazole (3.7 g, yield 71%) which contains 0.04% sulfone and 0.03% compound VI as within the limit of UV detection.

Example 2

A flask equipped with a stirrer is charged with ethyl acetate (140 ml). Under mixing, compound VI (7 g) is added, followed by 47% aqueous NaOH (4.6 g, 2.8 eq.). The flask is cooled to 0° C. Aqueous 9.4% active NaOCl (16.5 ml, d=1.16 g $ml^{-1}$, 1.27 eq.) is added dropwise over 30 min. The two-phase mixture is stirred at room temperature for 1.5 h. Aqueous 27% $Na_2S_2O_5$ (8 ml) is then added to the mixture. After stirring for several minutes, the phases are separated. The organic phase is washed with water, and the aqueous phase is washed twice with ethyl acetate. The organic phases are combined and concentrated to give 15 g of an oily residue. The oily residue is then taken up and precipitated from a 1:2 mixture of ethyl acetate:hexanes (15 ml). The precipitate is then filtered and washed to obtain pantoprazole (6.7 g, 92.3%) containing 0.19% sulfone and 0.08% compound VI within the limit of UV detection.

Example 3

A flask equipped with a stirrer is charged with ethyl acetate (50 ml). Under mixing, compound VI (10 g) is added, followed by 47% NaOH (8.72 g, 3.8 eq.). The flask is cooled to 0° C., and aqueous 11.1% active NaOCl (27.4 g, 1.5 eq.) is added dropwise over 20 min. The two-phase mixture is stirred at room temperature for 1.5 h. Aqueous 7% $Na_2S_2O_5$ (50 ml) is then added. After stirring for a few minutes, the phases are separated. The organic layer is washed with water, and the aqueous phase is washed twice with ethyl acetate. The organic phases are combined and concentrated to give 24 g of an oily residue. The residue is taken up and precipitated from toluene (15 ml). The precipitate is then filtered and washed to obtain pantoprazole (7.82 g, 75.2%) containing 0.05% sulfone and free of compound VI within the limit of UV detection.

Example 4

A flask equipped with a stirrer is charged with acetonitrile (0.6 L). Under mixing, compound VI (30 g) is added, followed by 18.8% aqueous NaOH (70 ml, 5.0 eq.). The flask is then cooled to −7° C. Aqueous 10.6% active NaOCl (70 ml, d=1.16, 1.4 eq.) is added dropwise over 45 min. The two-phase mixture is stirred at room temperature for 1.5 h. Aqueous $Na_2S_2O_5$ (120 ml) is added. The pH is then adjusted to 8 with 10% HCl solution (120 ml). The phases are separated. The organic layer is washed with water, and the aqueous phase is washed twice with acetonitrile. The organic phases are combined, dried over $MgSO_4$, and concentrated to one quarter of their original volume. Pantoprazole is precipitated from the concentrate and separated by filtration to yield pantoprazole (20.1 g, 64.8%) containing 0.04% compound VI and free of sulfone within the limit of UV detection.

Example 5

A 1 L flat bottom flask equipped with a stirrer is charged with acetonitrile (0.6 L). Under mixing compound VI (200 g) is added, followed by water (0.2 L), and NaOH pellets (88 g, 4.0 eq.). The flask is cooled to 5° C. Aqueous 9.4% active NaOCl (540 g, d=1.16, 1.25 eq.) is added dropwise over 40 min. The two-phase mixture is then stirred at room temperature for 40 min at 10° C. Solid $Na_2S_2O_5$ (6.6 g) is then added, and the mixture is stirred for another 0.5 h. The work up is finished by adjusting the pH to 8.5 with 32% HCl. A precipitate forms in the reaction mixture and is separated by filtration, washed with water, and dried to obtain pantoprazole (137.8 g, yield 66%) containing 0.02% sulfone and 0.01% compound VI within the limit of UV detection.

Example 6

The yield of Example 5 is further improved to 76% by using diisopropyl ether to aid the final precipitation without changing the impurity profile.

Example 7

A flask is charged with acetonitrile (0.1 L). Under mixing, compound VI (5 g) is added, followed by NaOH pellets (2.18 g, 4.0 eq.). The reactor is cooled to −7° C. A commercial 10.5% NaOCl solution (11.5 ml, 1.4 eq.) is diluted by a factor of 3 by adding water. The diluted NaOCl solution (34.5 ml) is added dropwise over 25 min. The two-phase mixture is stirred at room temperature for 2.5 h. Then, aqueous $Na_2S_2O_5$ (20 ml) is added. The pH of the aqueous phase is adjusted to 8 with 10% HCl (10 ml). The phases are then separated. The organic layer is washed with water, and the aqueous phase is washed twice with acetonitrile. The combined organic phases are combined, dried over magnesium sulfate ($MgSO_4$), and concentrated to one quarter of the original volume. A precipitate forms in the concentrate, which is separated by filtration to obtain pantoprazole (2.78 g, 53.8%) containing 0.07% compound VI and free of sulfone within the limited of UV detection.

Example 8

A flask is charged with isobutyl acetate (0.1 L). Under mixing, compound VI (5 g) is added, followed by 18.8% NaOH (11.5 ml, 4.9 eq.). The flask is cooled to −7° C. Then, aqueous 9.4% active NaOCl (11.5 ml, 1.24 eq.) is added dropwise over 15 min. The two-phase mixture is stirred at room temperature overnight, over which time a precipitate forms. Aqueous $Na_2S_2O_5$ (20 ml) is then added and the precipitate is redissolved. On standing, another precipitate forms in the mixture which is separated by filtration and dried to give pantoprazole (4.33 g, 83%) containing 0.4% compound VI and free of sulfone within the limit of UV detection.

Example 9

A flask equipped with a stirrer is charged with acetonitrile (40 ml). Under mixing, compound VI (5 g) is added followed by 2N NaOH (17.5 ml, 4.9 eq.). The flask is cooled to −10° C. A solution of N-chlorophthalimide (2.6 g, 1.1 eq.) in dimethylformamide (DMF) (10 ml) is added dropwise over 45 min. The two-phase mixture is stirred at room temperature over 1 h. Saturated aqueous $Na_2S_2O_5$ (20 ml) is then added, and the pH is adjusted to 8.5 with acetic acid. The phases are separated. The organic phase is washed with brine, and the aqueous phase is extracted twice with ethyl acetate. The organic phases are combined, dried, and evaporated to dryness. The residue is taken up in a mixture of ethyl acetate (10 ml), toluene (10 ml), and hexane (30 ml). On standing, a precipitate forms in the solution which is separated by filtration to give pantoprazole (5.13 g, 98%) containing 0.3% compound VI and free of sulfone within the limit of UV detection.

Example 10

Example 9 is repeated using N-chlorosaccharin as oxidant instead of N-chlorophthalimide, which results in a reduced yield of 55%.

Example 11

Example 9 is repeated using trichloroisocyanurate as oxidant instead of N-chlorophthalimide, which also results in a reduced yield of 90%.

Preparation of Pantoprazole Sodium Sesquihydrate

Example 12

Pantoprazole (5 g, 25.6 mmol), solid NaOH (0.574 g, 1.1 eq.), and methanol (MeOH) (0.5 ml) are added to toluene (25 ml) and stirred at room temperature. After 3 h, the mixture becomes clear and crystals begin to form. The mixture is left overnight. The crystals are filtered and dried at 50° C. under 10 mm Hg vacuum. The crystals are determined to be the sesquihydrate form of pantoprazole sodium by powder X-ray diffraction (PXRD) and are found to have a water content of 7.2% by Karl Fischer analysis. Yield: 90%.

Example 13

Pantoprazole (20 g), solid NaOH (2.089 g, 1 eq.), and water (3.3 ml) are added to ethyl acetate (200 ml) and stirred at room temperature. The mixture becomes clear. Crystals begin to form after 30 min. The crystals are filtered after 5 h and dried at 50° C. under 10 mm Hg vacuum. The crystals (20.5 g) are determined to be the sesquihydrate form of pantoprazole sodium by PXRD and are found to have a water content of 6.52% by Karl Fisher analysis. Yield: 92%.

Example 14

Pantoprazole (5 g, 25.6 mmol) and 47% NaOH (1 eq.) are added to acetonitrile (25 ml) and stirred at room temperature. After 3 h, the mixture becomes clear, and crystals begin to form. The mixture is allowed to stand overnight. The crystals are filtered and dried at 50° C. under 10 mm Hg vacuum. The crystals are determined to be the sesquihydrate form of pantoprazole sodium by PXRD and are found to have a water content of 7.0% by Karl Fisher analysis. Yield: 95%.

Example 15

To a suspension of compound VI (7.1 g, 19.4 mmol) in ethyl acetate (140 ml), a mixture of NaOCl (9.4% active, 13 ml, 19.4 mmol) and 20% NaOH (3.3 ml, 19.4 mmol) is added dropwise with stirring at −10° C. over 15 min. The two-phase mixture is stirred for an additional 30 min at the same temperature. An HPLC chromatogram of a sample of the reaction mixture shows that 8% of the starting material remains unreacted. Additional NaOCl (9.4% active, 1.2 ml, 1.7 mmol) is added and the reaction mixture is stirred for another 45 min at −1° C. A 7% aqueous solution of $Na_2S_2O_5$ (50 ml) is then added to the reaction mixture at −10° C. with stirring. Then, the mixture is heated to room temperature and stirred for an additional 30 min. The phases are separated, and the organic phase is evaporated under vacuum to dryness. The residue is taken up in ethyl acetate (70 ml), and 38% aqueous NaOH (2.1 g, 19.4 mmol) is added to the solution. The solution is stirred for 6 h at room temperature, over which time a precipitate forms in the bottom of the flask. The precipitate is filtered and washed with ethyl acetate giving, after drying, pantoprazole (6.3 g, 71%) containing 0.06% sulfone within the limit of UV detection.

The pantoprazole is determined to be in the sesquihydrate form by PXRD and determined to have a 6.5% water content by Karl Fisher analysis.

Example 16

A flask was charged with acetonitrile (60 ml). The flask was cooled to 0° C. and then NaOCl (72.6 g, 9.82% active, 1.25 eq.), NaOH pellets (13.1 g, 4 eq.), and compound VI (30 g) were added to the flask. The mixture was stirred at 0° C. for 4 h. During that time, pantoprazole sodium precipitated. The recovered precipitate was recrystallized in ethyl acetate involving hot filtration of inorganic salts. Pantoprazole sodium that was free of compound VI and the sulfone within the limit of detection was recovered in 85% yield.

The yield and purity results obtained in Examples 1 through 11, 15 and 16 are summarized in Table 1

TABLE 1

| Ex. | % Yield | % Sulfone | % Sulfide |
|---|---|---|---|
| 1 | 71 | 0.04 | 0.03 |
| 2 | 92.3 | 0.19 | 0.08 |
| 3 | 75.2 | 0.05 | n.d.[a] |
| 4 | 64.8 | n.d. | 0.04 |
| 5 | 66.0 | 0.02 | 0.01 |
| 6 | 76.0 | — | — |
| 7 | 53.8 | n.d. | 0.07 |
| 8 | 83 | n.d. | 0.4 |
| 9 | 98 | n.d. | 0.3 |
| 10 | 55 | — | — |
| 11 | 90 | — | — |
| 15 | 71[b] | 0.06 | — |
| 16 | 85[b] | n.d. | n.d. |

[a] not detected
[b] Yield reported for pantoprazole sodium

Preparation of Chlorinated Derivatives of Pantoprazole

Example 17

Pantoprazole sodium (5.0 g, 12 mmol) was dissolved in 100 ml of acetonitrile. Then 4 ml of 20% aq. sodium hydroxide (4 ml, 1.8 eq.) was added followed by addition of sodium hypochlorite (17 ml, 9%, 24 mmol, 1.8 eq.) dropwise at room temperature. The mixture was stirred for additional 12 hours and then 10% aq. sodium metabisulfite solution was added to pH 8-9, and the mixture was stirred at room temperature for 1 hour. After phase separation, acetonitrile was evaporated under vacuum at room temperature. The products were separated by flash column chromatography ($SiO_2$, ethyl acetate) giving compound IV (200 mg) and compound V (200 mg).

Compound IV: $^1$H-NMR (600 MHz, $CD_3CN$) δ (ppm): 3.86 (s, 3H), 3.88 (s, 3H), 6.63 (s, 1H), 6.83 (t, 1H, $J_{H-F}$=74.5 Hz, $J_{C-F}$=257.5 Hz), 7.04 (d, 1H, J=5.6 Hz), 7.20 (dd, 1H, J=1.8 and 8.4 Hz), 7.43 (br, 1H), 7.66 (br, 1H), 8.32 (d, 1H, J=5.6 Hz); $^{13}$C-NMR (300 MHz, $CD_3CN$), δ(ppm): 56.88, 62.33, 69.72, 107.80, 110.52, 117.73, 118.03, 145.60, 146.86, 146.94, 147.67, 148.96, 149.07, 154.33, 160.11; MS (FAB+), m/z 418.031 (MH+ ion, calculated for $C_{16}H_{15}N_3O_4ClF_2S$: 418.0435; the m/z 420 isotope ion supports presence of one Cl atom).

Compound V: $^1$H-NMR (600 MHz, $CD_3CN$) δ (ppm): 3.888 (s, 3H), 3.894 (s, 3H), 6.76 (t, 1H, $J_{H-F}$=75 Hz, $J_{C-F}$=256.5 Hz), 7.06 (d, 1H, J=5.4 Hz), 7.07 (dd, 1H, J=2.4 and 9.0 Hz), 7.43 (dd, 1H, J=0.6 and 2.4 Hz), 7.67 (dd, 1H, J=0.6 and 2.9 Hz), 8.03 (d, 1H, J=5.4 Hz); $^{13}$C-NMR (300 MHz, $CD_3CN$), δ (ppm): 57.11, 61.60, 98.07, 108.65, 111.83, 117.25, 118.11, 120.27, 141.54, 143.50, 143.81, 146.34, 146.51, 148.61, 150.66, 161.37; MS (Cl+), m/z 434.0380 (MH+ ion, calculated for $C_{16}H_{15}N_3O_5ClF_2S$: 434.0425; the m/z 436 isotope ion supports presence of one Cl atom).

Having thus described the invention with respect to certain preferred embodiments and further illustrated it with examples, those skilled in the art may come to appreciate substitutions and equivalents that albeit not expressly described are taught and inspired by this invention.

What is claimed is:

1. 6-(Difluoromethoxy)-2-[(3,4-dimethoxypyridin-2-yl)methylsulfinyl]-1H-benzo[d]imidazole containing less than about 0.2% total impurities as determined by percentage area HPLC.

2. The 6-(difluoromethoxy)-2-[(3,4-dimethoxypyridin-2-yl)methylsulfinyl]-1H-benzo[d]imidazole of claim 1 containing less than about 0.1% total impurities as determined by percentage area HPLC.

3. The 6-(difluoromethoxy)-2-[(3,4-dimethoxypyridin-2-yl)methylsulfinyl]-1H-benzo[d]imidazole of claim 2 containing less than about 0.05% total impurities as determined by percentage area HPLC.

4. 6-(difluoromethoxy)-2-[(3,4-dimethoxypyridin-2-yl)methylsulfinyl]-1H-benzo[d]imidazole containing less than about 0.2% of the following sulfone as determined by percentage area HPLC.

5. The 6-(difluoromethoxy)-2-[(3,4-dimethoxypyridin-2-yl)methylsulfinyl]-1H-benzo[d]imidazole of claim 4 containing less than about 0.15% of the following sulfone as determined by percentage area HPLC.

6. 6-(difluoromethoxy)-2-[(3,4-dimethoxypyridin-2-yl)methylsulfinyl]-1H-benzo[d]imidazole sesquihydrate containing less than about 0.2% total impurities as determined by percentage area HPLC.

7. The 6-(difluoromethoxy)-2-[(3,4-dimethoxypyridin-2-yl)methylsulfinyl]-1H-benzo[d]imidazole sesquihydrate of claim 6 containing less than about 0.1% total impurities as determined by percentage area HPLC.

8. The 6-(difluoromethoxy)-2-[(3,4-dimethoxypyridin-2-yl)methylsulfinyl]-1H-benzo[d]imidazole sesquihydrate of claim 7 containing less than about 0.05% total impurities as determined by percentage area HPLC.

* * * * *